United States Patent [19]

Drabek et al.

[11] Patent Number: 4,939,257
[45] Date of Patent: Jul. 3, 1990

[54] PHENOXYPHENYLTHIOUREAS

[75] Inventors: Jozef Drabek, Oberwil, Switzerland; Manfred Böger, Weil am Rhein, Fed. Rep. of Germany

[73] Assignee: Ciba-Geigy Corporation, Ardsley, N.Y.

[21] Appl. No.: 248,304

[22] Filed: Sep. 21, 1988

Related U.S. Application Data

[60] Continuation of Ser. No. 93,433, Sep. 4, 1987, abandoned, which is a continuation of Ser. No. 616,372, Jun. 1, 1984, abandoned, which is a continuation of Ser. No. 344,580, Feb. 1, 1982, abandoned, which is a division of Ser. No. 185,078, Sep. 8, 1980, Pat. No. 4,328,247.

[30] Foreign Application Priority Data

Sep. 19, 1979 [CH] Switzerland .......................... 8474/79
Sep. 21, 1979 [CH] Switzerland .......................... 8567/79
Nov. 12, 1979 [CH] Switzerland ........................ 10084/79
Nov. 12, 1979 [CH] Switzerland ........................ 10085/79
Jul. 18, 1980 [CH] Switzerland .......................... 5541/80

[51] Int. Cl.$^5$ .................. C07C 157/07; C07C 157/09
[52] U.S. Cl. ..................................................... 564/28
[58] Field of Search .................... 564/28, 29; 558/4, 5

[56] References Cited

U.S. PATENT DOCUMENTS

| | | | |
|---|---|---|---|
| 3,781,290 | 12/1973 | Spaun et al. ...................... | 564/28 X |
| 3,799,759 | 3/1974 | Martin et al. ...................... | 564/28 X |
| 3,933,814 | 1/1976 | Haberkorn et al. ............... | 564/28 X |
| 4,066,695 | 1/1978 | Cohen et al. ...................... | 558/4 |
| 4,328,247 | 5/1982 | Drabek et al. ...................... | 558/4 X |
| 4,328,248 | 5/1982 | Boger et al. ...................... | 558/4 X |
| 4,404,225 | 9/1983 | Boger et al. ...................... | 564/28 X |

Primary Examiner—Robert V. Hines
Attorney, Agent, or Firm—Kevin T. Mansfield; Edward McC. Roberts

[57] ABSTRACT

The invention relates to N-phenoxyphenylisothioureas of the formula

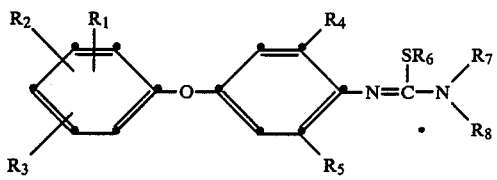

wherein each of $R_1$, $R_2$ and $R_3$ is hydrogen, halogen, $C_1$-$C_4$alkyl, $C_1$-$C_4$alkoxy, trifluoromethyl or nitro, each of $R_4$ and $R_5$ is $C_2$-$C_4$alkyl, $R_6$ is $C_1$-$C_6$alkyl, $C_3$-$C_6$alkenyl or $C_3$-$C_5$alkynyl, $R_7$ is $C_1$-$C_{10}$alkyl, $C_3$-$C_5$alkenyl or $C_3$-$C_6$cycloalkyl, and $R_8$ is hydrogen or $C_1$-$C_{10}$alkyl. The invention further relates to the production of these compounds and their use in pest control, as well as to phenoxyphenylthioureas as intermediates for the production of the N-phenoxyphenylisothioureas of the invention.

8 Claims, No Drawings

PHENOXYPHENYLTHIOUREAS

This application is a continuation of application Ser. No. 093,433, filed Sept. 4, 1987, abandoned, which is a continuation of application Ser. No. 616,372, filed June 1, 1984, abandoned, which is a continuation of application Ser. No. 344,580, filed Feb. 1, 1982, abandoned, which is a divisional of application Ser. No. 185,078, filed Sept. 8, 1980, now Pat. No. 4,328,247.

The present invention relates to N-phenoxyphenylisothioureas, the production thereof, pesticidal compositions containing them, and use thereof for controlling pests of animals and plants.

The N-phenoxyphenylisothioureas have the formula

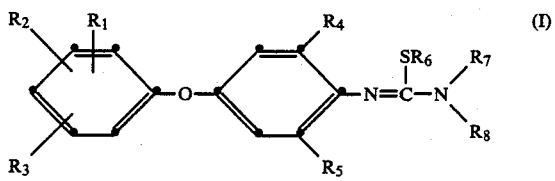

wherein each of $R_1$, $R_2$ and $R_3$ is hydrogen, halogen, $C_1$–$C_4$alkyl, $C_1$–$C_4$alkoxy, trifluoromethyl or nitro, each of $R_4$ and $R_5$ is $C_2$–$C_4$alkyl, $R_6$ is $C_1$–$C_6$alkyl, $C_3$–$C_6$alkenyl or $C_3$–$C_5$alkynyl, $R_7$ is $C_1$–$C_{10}$alkyl, $C_3$–$C_5$alkenyl or $C_3$–$C_6$cycloalkyl, and $R_8$ is hydrogen or $C_1$–$C_{10}$alkyl.

Halogen in the above definition denotes fluorine, chlorine, bromine or iodine, with chlorine being preferred.

Alkyl, alkoxy, alkenyl and alkynyl groups $R_1$ to $R_8$ can be straight chain or branched. Examples of such groups comprise methyl, methoxy, ethyl, propyl, isopropyl, n-butyl, isobutyl, sec-butyl, tert-butyl, n-pentyl, n-hexyl, n-heptyl, n-octyl, n-nonyl, n-decyl and their isomers, allyl, methallyl, and propargyl.

Preferred cycloalkyl groups $R_7$ are cyclopropyl and cyclohexyl.

Preferred compounds on account of their activity are those of the formula I wherein $R_1$ is hydrogen, chlorine, methoxy, trifluoromethyl or nitro, each of $R_2$ and $R_3$ is hydrogen or chlorine, each of $R_4$ and $R_5$ is ethyl, isopropyl, isobutyl, sec-butyl or tert-butyl, $R_6$ is $C_1$–$C_6$alkyl, allyl or propargyl, $R_7$ is $C_1$–$C_6$alkyl, cyclopropyl or cyclohexyl, and $R_8$ is hydrogen.

Especially preferred compounds, however, are those of the formula I wherein $R_1$ is hydrogen, chlorine or trifluoromethyl, $R_2$ is hydrogen or chlorine, $R_3$ is hydrogen, each of $R_4$ and $R_5$ is isopropyl, or $R_4$ is ethyl and $R_5$ is sec-butyl, $R_6$ is methyl, $R_7$ is tert-butyl or isopropyl, and $R_8$ is hydrogen.

The compounds of formula I also exist in the form of acid addition salts, e.g. mineral salts, and can be used in the form of their salts in the practice of this invention. Accordingly, the invention is to be construed as comprising both the free compounds of formula I and their non-toxic acid addition salts.

The compounds of the formula I can be converted to their acid addition salts by procedures known per se. Suitable acids for forming addition salts are for example: hydrochloric acid, hydrobromic acid, hydriodic acid, nitric acid, phosphoric acid, sulfuric acid, acetic acid, propionic acid, butyric acid, valeric acid, oxalic acid, malonic acid, succinic acid, malic acid, maleic acid, fumaric acid, lactic acid, tartaric acid, citric acid, benzoic acid, phthalic acid, cinnamic acid and salicyclic acid.

The compounds of formula I can be obtained by methods analogous to known ones, by reacting e.g. a thiourea of the formula

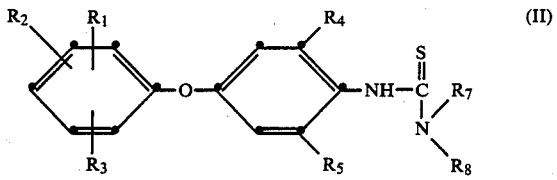

with a halide of the formula

in which formulae II and III above $R_1$ to $R_8$ are as defined for formula I and Hal is a halogen atom, especially a chlorine or bromine atom.

The process is conveniently carried out in the temperature range from 0° to 100° C., under normal or slightly elevated pressure, and preferably in the presence of a solvent or diluent which is inert to the reactants. Examples of suitable solvents or diluents are ethers and ethereal compounds such as diethyl ether, diisopropyl ether, dioxane and tetrahydrofurane; aromatic hydrocarbons such as benzene, toluene and xylenes; and ketones such as acetone, methyl ethyl ketone and cyclohexanone.

The starting compounds of the formula 11 are new. They can be readily obtained from known precursors by reacting e.g. an isothiocyanate of the formula IV

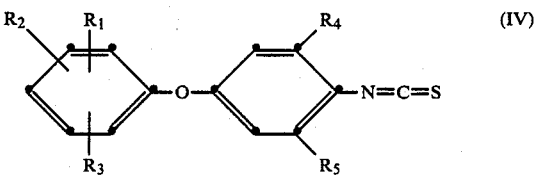

with an amine of the formula V

in which formulae IV and V above $R_1$ to $R_5$ and $R_7$ are as previously defined (cf. Example 1).

The process for obtaining the starting materials of formula II is preferably carried out in the presence of a solvent or diluent which is inert to the reactants, in the temperature range from 0° to 100° C. and under normal pressure. Suitable solvents and diluents for this process are those specified above as suitable for the process for obtaining the final products of formula I.

The compounds of formula I and the starting materials of formula II are suitable for controlling pests of animals and plants.

In particular, the compounds of formulae I and II are suitable for controlling insects, phytopathogenic mites and ticks, e.g. of the order Lepidcptera, Coleoptera, Homoptera, Diptera, Acarina, Thysanoptera, Orthoptera, Anoplura, Siphonaptera, Mallophaga, Thysanura, Isoptera, Psocoptera and Hymenoptera.

In particular, the compounds of formulae I and II are suitable for controlling plant-destructive insects, especially plant-destructive feeding insects, in ornamentals and useful plants, preferably in cotton plantations (e.g.

*Spodoptera littoralis* and *Heliothis virescens*) and in vegetables (e.g. *Leptinotarsa decemlineata*).

Compounds of formulae I and II are also very effective against flies, e.g. *Musca domestica* and mosquito larvae.

The acaracidal activity of the compounds of formula I also extends to both plant-destructive acarids (mites e.g. of the families Tetranychidae, Tarsonemidae, Eriophydae, Tyroglyphidae and Glycyphagidas) and against ectoparasitic acarids (mites and ticks e.g. of the families Ixodidae, Argasidae, Sarcoptidae and Dermanyssidae) which are harmful to productive livestock.

Compounds of the formulae I and II are also combined with particular advantage with substances which exert a synergistic or potentiating effect. Examples of such compounds include: piperonyl butoxide, propynyl ether, propynyl oximes, propynyl carbamates and propynyl phosphates, 2-(3,4-methylenedioxyphenoxy)-3,6,9-trioxaundecane (Sesamex or Sesoxane), S,S,S-tributylphosphorotrithioate, 1,2-methylenedioxy-4(2-(octylsulfinyl)-propyl)-benzene.

The compounds of formulae I and II can be employed in known manner and in unmodified form or together with the adjuvants conventionally used in the art of formulation, e.g. emulsifiable concentrates, suspension concentrates, directly sprayable or dilutable solutions, dilute emulsions, wettable powders, soluble powders, dusts, granules, and also micro-encapsulations in polymer substances and the like. The methods of application, such as spraying, atomising, dusting, scattering or pouring, depend entirely on the end-use requirements, in which connection it must be ensured that the biological activity of the compounds of formulae I or II is not substantially influenced by the method of application or by the nature and amount of the adjuvants employed for preparing the formulation.

The preparations are produced in known manner, for example by intimately mixing and/or grinding the active ingredients with extenders, i.e. with solvents or solid carriers, and optionally with the use of surface-active substances (surfactants). Suitable solvents are aromatic hydrocarbons, preferably the fractions $C_8$ to $C_{12}$, i.e. xylene mixtures up to substituted naphthalenes, aliphatic hydrocarbons such as cyclohexane or paraffins, alcohols and glycols, as well as ethers and esters thereof, strongly polar solvents, such as dimethyl sulfoxide or dimethyl formamide, and also water. The solid carriers used, e.g. for dusts and dispersible powders, are mostly natural mineral fillers. For chemical purposes, suitable solid carriers are in particular calcite, talcum, kaolinite, montmorillonite and attapulgite. In order to improve the physical properties, it is also possible to use highly dispersed silicic acids or highly dispersed absorbent polymers. Suitable granulated carriers are porous types, e.g. pumice, broken brick, sepiolite and bentonite; and suitable nonsorbent carriers are materials such as calcite or sand. In addition, it is also possible to use a large number of pregranulated materials of inorganic or organic nature, extending from dolomite to pulverised nutshells or corncobs.

Depending on the polarity of the compound of the formula I or II to be formulated, suitable surface-active substances are nonionic, cationic and/or anionic surfactants having good emulsifying, dispersing and wetting properties.

Examples of suitable anionic surfactants are: quaternary ammonium compounds such as cetyltrimethylammonium bromide. Examples of suitable anionic surfactants are: soaps, salts of aliphatic monoesters of sulfuric acid, such as sodium lauryl sulfate, salts of sulfonated aromatic compounds, for example sodium dodecylbenzenesulfonate, sodium, calcium and ammonium ligninsulfonate, butylnaphthalenesulfonate and a mixture of the sodium salts of diisopropyl- and triisopropylnaphthalenesulfonate. Examples of suitable non-ionic surfactants are the condensation products of ethylene oxide with fatty alcohols, for example oleyl alcohol or cetyl alcohol, or with alkylphenols, such as octylphenol, nonylphenol and octylcresol. Other non-ionic compounds are the partial esters derived from long-chain fatty acids and hexite anhydrides, and the condensation products of these partial esters with ethylene oxide, or lecithins.

The non-ionic, anionic and cationic surfactants commonly used in the art of formulation are described, inter alia, in the following publications: "Mc Cutcheon's Detergents and Emulsfiers Annual", MC Publishing Corp., Ringewood, N.J.; Sisely and Wood, "Encyclopedia of Surface Active Agents", Chemical Publishing Co., N.Y.

The formulations as a rule contain 0.1 to 99%, especially 0.1 to 95%, of compound of the formula I or II, and at least 0 to 25% of a surfactant, as well as 1 to 99.9% of a solid or liquid adjuvant.

The formulations can also contain additives such as stabilisers, antifoams, viscosity regulators, binders, adhesives, and also fertilisers, to produce special effects The compounds (active ingredients) of the formula I or II can be formulated for example as follows: (throughout, percentages are by weight)

FORMULATION EXAMPLES FOR LIQUID ACTIVE INGREDIENTS OF THE FORMULA I OR II

| | Emulsifiable concentrates | |
|---|---|---|
| (a) | active ingredient | 20% |
| | calcium dodecylbenzenesulfonate | 5% |
| | castor oil polyglycol ether (36 moles of ethylene oxide) | 5% |
| | xylene mixture | 70%; |
| (b) | active ingredient | 40% |
| | calcium dodecylbenzenesulfonate | 8% |
| | tributylphenolpolyglycol ether (30 moles of ethylene oxide) | 12% |
| | cyclohexanone | 15% |
| | xylene mixture | 25%; |
| (c) | active ingredient | 50% |
| | tributylphenolpolyglycol ether | 4.2% |
| | calcium dodecylbenzenesulfonate | 5.8% |
| | cyclohexanone | 20% |
| | xylene mixture | 20%. |

Emulsions of any required concentration can be produced from such concentrates by dilution with water.

| | Solutions | |
|---|---|---|
| (a) | active ingredient | 80% |
| | ethylene glycol monomethyl ether; | 20% |
| (b) | active ingredient | 10% |
| | polyethylene glycol 400 | 70% |
| | N-methyl-2-pyrrolidone; | 20% |
| (c) | active ingredient | 5% |
| | epoxidised vegetable oil | 1% |
| | ligroin (boiling range 160–190° C.); | 94% |
| (d) | active ingredient | 95% |
| | epoxidised vegetable oil | 5%. |

These solutions are suitable for application in the form of microdrops.

| Granules | | |
|---|---|---|
| (a) | active ingredient | 5% |
| | kaolin (0.2–0.8 mm) | 94% |
| | highly dispersed silicic acid | 1% |
| (b) | active ingredient | 10% |
| | attapulgit | 90%. |

The active ingredient is dissolved in methylene chloride, the solution is sprayed onto the carrier, and the solvent is subsequently evaporated off in vacuo.

| Dusts | | |
|---|---|---|
| (a) | active ingredient | 2% |
| | highly dispersed silicic acid | 1% |
| | talcum | 97% |
| (b) | active ingredient | 5% |
| | highly dispersed silicic acid | 5% |
| | kaolin (finely divided) | 90%. |

Dusts which are ready for use are obtained by intimately mixing the carriers with the active ingredients.

FORMULATION EXAMPLES FOR SOLID ACTIVE INGREDIENTS OF THE FORMULA I OR II

| Wettable powders | | |
|---|---|---|
| (a) | active ingredient | 20% |
| | sodium ligninsulfonate | 5% |
| | sodium laurylsulfate | 3% |
| | silicic acid | 5% |
| | kaolin | 67% |
| (b) | active ingredient | 60% |
| | sodium ligninsulfonate | 5% |
| | sodium diisobutylnaphthalenesulfonate | 6% |
| | octylphenol polyglycol ether | 2% |
| | (7–8 moles of ethylene oxide) | |
| | highly dispersed silicic acid | 27%. |

The active ingredient is thoroughly mixed with the adjuvants and the mixture is thoroughly ground in a suitable mill, affording wettable powders which can be diluted with water to give suspensions of the desired concentration.

| Emulsifiable concentrate | |
|---|---|
| active ingredient | 10% |
| octylphenol polyglycol ether | 3% |
| (4–5 moles of ethylene oxide) | |
| calcium dodecylbenzenesulfonate | 3% |
| castor oil polyglycol ether | 4% |
| (36 moles of ethylene oxide) | |
| cyclohexanone | 30% |
| xylene mixture | 50%. |

Emulsions of any required concentration can be obtained from this concentrate by dilution with water

| Dusts | | |
|---|---|---|
| (a) | active ingredient | 5% |
| | talcum | 95% |
| (b) | active ingredient | 8% |
| | kaolin (finely divided) | 92%. |

Dusts which are ready for use are obtained by mixing the active ingredient with the carriers, and grinding the mixture in a suitable mill.

| Extruder granulate | |
|---|---|
| active ingredient | 10% |
| sodium ligninsulfonate | 2% |
| carboxymethylcellulose | 1% |
| kaolin (finely divided) | 87%. |

The active ingredient is mixed and ground with the adjuvants, and the mixture is subsequently moistened with water. The mixture is extruded and then dried in a stream of air.

| Coated granulate | |
|---|---|
| active ingredient | 3% |
| polyethylene glycol 200 | 3% |
| kaolin (0.3–0.8 mm) | 94%. |

The finely ground active ingredient is uniformly applied, in a mixer, to the kaolin moistened with polyethylene glycol. Non-dusty coated granulates are obtained in this manner.

| Suspension concentrate | |
|---|---|
| active ingredient | 40% |
| ethylene glycol | 10% |
| nonylphenol polyglycol ether | 6% |
| (15 moles of ethylene oxide) | |
| sodium ligninsulfonate | 10% |
| carboxymethylcellulose | 1% |
| formalin (37% formaldehyde solution) | 0.2% |
| silicone oil in the form of a 75% emulsion | 0.8% |
| water | 32%. |

The finely ground active ingredient is intimately mixed with the adjuvants, giving a suspension concentrate from which suspensions of any desired concentration can be obtained by dilution with water.

EXAMPLE 1

(a) Production of 2,6-diisopropyl-4-phenoxyaniline 48.9 g of phenol are dissolved in 500 ml of xylene, and to this solution are added 30.2 g of pulverised potassium hydroxide in an atmosphere of nitrogen. The reaction mixture is stirred and heated to boiling point, while continuously distilling off the water that is formed. After addition of 0.6 g of copper chloride and 100 g of 2,6-diisopropyl-4-bromoaniline, the mixture is stirred for 8 hours at 150°–155° C., then cooled, and filtered with suction. The filtrate is washed with 15% sodium hydroxide solution (150 ml) and with two 150 ml portions of water. The organic phase is separated and dried over sodium sulfate. The solvent is removed by distillation and the product is distilled, affording the compound of the formula

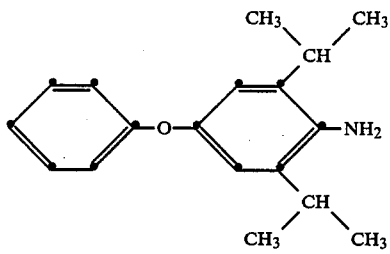

with a boiling point of 103°–104° C./0.01 torr and a melting point of 71°–72° C. (after recrystallisation from hexane).

The following anilines are also obtained in analogous manner:

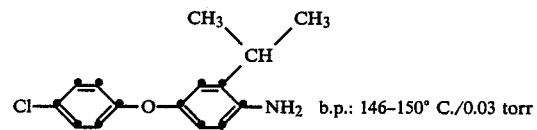 b.p.: 146–150° C./0.03 torr

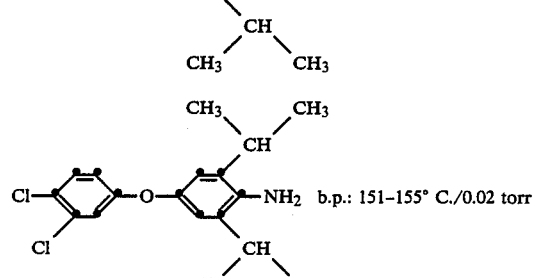 b.p.: 151–155° C./0.02 torr

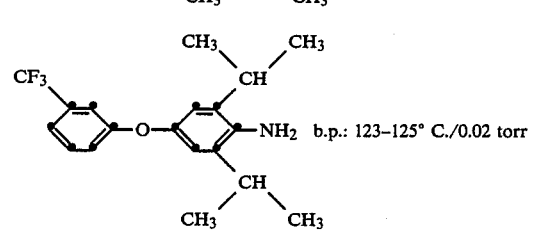 b.p.: 123–125° C./0.02 torr

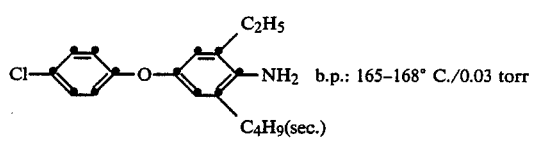 b.p.: 165–168° C./0.03 torr

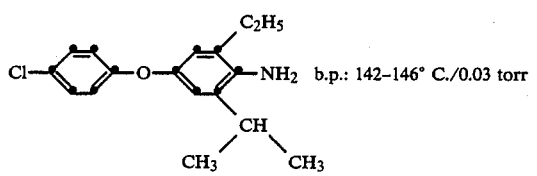 b.p.: 142–146° C./0.03 torr

-continued

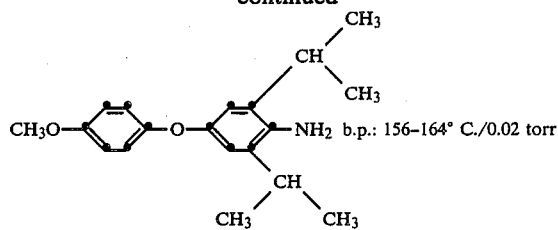 b.p.: 156–164° C./0.02 torr

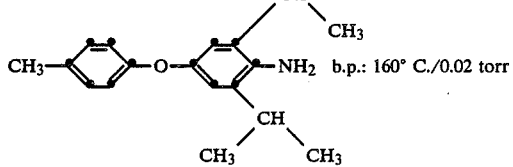 b.p.: 160° C./0.02 torr (b) Production of N-(2,6-diisopropyl-4-phenoxyphenyl)isothioscyanate 8.9 g of thiophosgene and 13.7 g of calcium carbonate are stirred in 60 ml of methylene chloride and 35 ml of water. Then 17.4 g of 2,6-diisoproypl-4-phenoxyaniline are added dropwise at 0° to 5° C. to this mixture. The reaction mixture is brought to the boil and stirred for 2 hours at reflux. After it has cooled, the mixture is filtered. The organic phase is separated from the filtrate, washed with two 50 ml portions of water, dried over sodium sulfate and concentrated. The crude product (oil) is used without purification for further reaction.

The following compounds are obtained in analogous manner:

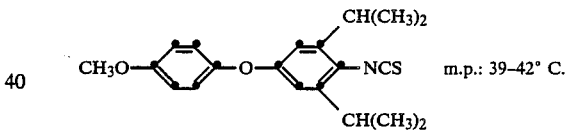 m.p.: 39–42° C.

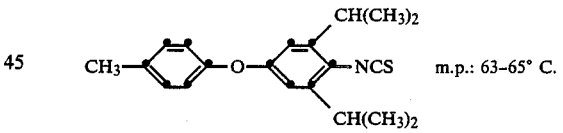 m.p.: 63–65° C.

(c) Production of compounds of the formula II 19.2 g of N-2,6-diisopropyl-4-phenoxyphenylisothiocyanate are diluted with 10 ml of toluene and then 13.8 g of tert-butylamine are added. The reaction mixture is then stirred for 12 hours at 20°–25° C. The reaction mixture is concentrated and the residue is recrystallised from hexane, affording the compound of the formula

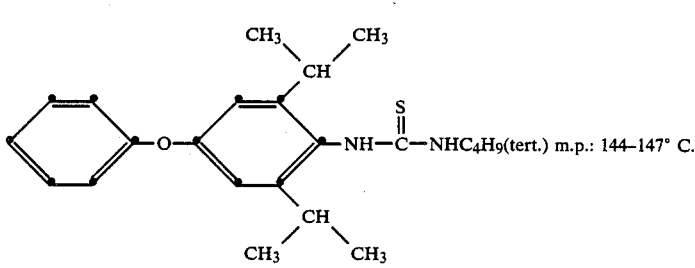 m.p.: 144–147° C.

The following compounds are obtained in analogous manner:

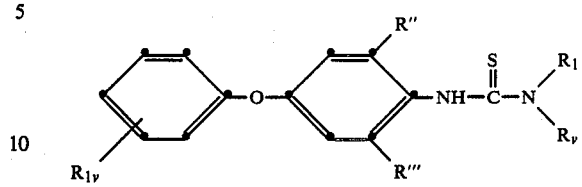

| R' | R" | R'" | R$^{IV}$ | R$^V$ | |
|---|---|---|---|---|---|
| C$_4$H$_9$(tert.) | C$_3$H$_{7(i)}$ | C$_3$H$_{7(i)}$ | 4-Cl | H | m.p.: 146–148° C. |
| C$_4$H$_9$(tert.) | C$_3$H$_{7(i)}$ | C$_3$H$_{7(i)}$ | 3-CF$_3$ | H | m.p.: 83–85° C. |
| C$_4$H$_9$(tert.) | C$_2$H$_5$ | C$_4$H$_9$(sec.) | 4-Cl | H | m.p.: 91–92° C. |
| C$_4$H$_9$(tert.) | C$_2$H$_5$ | C$_3$H$_{7(i)}$ | 4-Cl | H | m.p.: 127–129° C. |
| C$_3$H$_{7(i)}$ | C$_3$H$_{7(i)}$ | C$_3$H$_{7(i)}$ | 4-OCH$_3$ | H | m.p.: 187° C. |
| C$_4$H$_9$(tert.) | C$_3$H$_{7(i)}$ | C$_3$H$_{7(i)}$ | 4-OCH$_3$ | H | m.p.: 178° C. |
| C$_4$H$_9$(tert.) | C$_3$H$_{7(i)}$ | C$_3$H$_{7(i)}$ | 4-CH$_3$ | H | m.p.: 168–170° C. |
| C$_3$H$_{7(i)}$ | C$_3$H$_{7(i)}$ | C$_3$H$_{7(i)}$ | 4-CH$_3$ | H | m.p.: 146–147° C. |
| CH$_3$ | C$_3$H$_{7(i)}$ | C$_3$H$_{7(i)}$ | H | H | m.p.: 130–131° C. |
| C$_2$H$_5$ | C$_3$H$_{7(i)}$ | C$_3$H$_{7(i)}$ | H | H | m.p.: 148–149° C. |
| C$_3$H$_{7(n)}$ | C$_3$H$_{7(i)}$ | C$_3$H$_{7(i)}$ | H | H | m.p.: 121–122° C. |
| C$_3$H$_{7(i)}$ | C$_3$H$_{7(i)}$ | C$_3$H$_{7(i)}$ | H | H | m.p.: 160–161° C. |
| C$_4$H$_{9(n)}$ | C$_3$H$_{7(i)}$ | C$_3$H$_{7(i)}$ | H | H | m.p.: 117–119° C. |
| C$_4$H$_{9(i)}$ | C$_3$H$_{7(i)}$ | C$_3$H$_{7(i)}$ | H | H | m.p.: 152–153° C. |
| C$_4$H$_9$(sec.) | C$_3$H$_{7(i)}$ | C$_3$H$_{7(i)}$ | H | H | m.p.: 157–158° C. |
| C$_5$H$_{11(n)}$ | C$_3$H$_{7(i)}$ | C$_3$H$_{7(i)}$ | H | H | m.p.: 121–122° C. |
| CH$_3$ | C$_3$H$_{7(i)}$ | C$_3$H$_{7(i)}$ | H | CH$_3$ | m.p.: 149–150° C. |
| C$_2$H$_5$ | C$_3$H$_{7(i)}$ | C$_3$H$_{7(i)}$ | H | C$_2$H$_5$ | m.p.: 161–162° C. |
| C$_3$H$_{7(n)}$ | C$_3$H$_{7(i)}$ | C$_3$H$_{7(i)}$ | H | C$_3$H$_{7(n)}$ | m.p.: 152–153° C. |
| C$_4$H$_{9(n)}$ | C$_3$H$_{7(i)}$ | C$_3$H$_{7(i)}$ | H | C$_4$H$_{9(n)}$ | m.p.: 153–154° C. |
| C$_4$H$_9$(sec.) | C$_3$H$_{7(i)}$ | C$_3$H$_{7(i)}$ | 4-CH$_3$ | H | m.p.: 156–157° C. |
| CH$_3$ | C$_3$H$_{7(i)}$ | C$_3$H$_{7(i)}$ | 4-OCH$_3$ | H | m.p.: 156–157° C. |
| C$_2$H$_5$ | C$_3$H$_{7(i)}$ | C$_3$H$_{7(i)}$ | 4-OCH$_3$ | H | m.p.: 154–155° C. |
| C$_3$H$_{7(n)}$ | C$_3$H$_{7(i)}$ | C$_3$H$_{7(i)}$ | 4-OCH$_3$ | H | m.p.: 155–156° C. |
| C$_4$H$_{9(i)}$ | C$_3$H$_{7(i)}$ | C$_3$H$_{7(i)}$ | 4-OCH$_3$ | H | m.p.: 112–113° C. |
| C$_4$H$_9$(sec.) | C$_3$H$_{7(i)}$ | C$_3$H$_{7(i)}$ | 4-OCH$_3$ | H | m.p.: 170–171° C. |
| C$_7$H$_{15(n)}$ | C$_3$H$_{7(i)}$ | C$_3$H$_{7(i)}$ | 4-OCH$_3$ | H | m.p.: 95–98° C. |
| C$_3$H$_{7(i)}$ | C$_3$H$_{7(i)}$ | C$_3$H$_{7(i)}$ | 4-OCH$_3$ | H | m.p.: 187° C. |
| —CH(CH$_2$CH$_2$) (cyclopropyl) | CH$_3$ | C$_3$H$_{7(i)}$ | 4-Cl | H | m.p.: 143–145° C. |
| —CH(CH$_2$CH$_2$) (cyclopropyl) | C$_2$H$_5$ | C$_3$H$_{7(i)}$ | 4-Cl | H | m.p.: 80–85° C. |
| CH$_3$ | C$_2$H$_5$ | C$_4$H$_9$(sec.) | 4-Cl | H | m.p.: 109–110° C. |
| C$_3$H$_{7(i)}$ | C$_2$H$_5$ | C$_4$H$_9$(sec.) | H | H | m.p.: 107–110° C. |
| C$_4$H$_9$(tert.) | C$_2$H$_5$ | C$_4$H$_9$(sec.) | H | H | m.p.: 97–100° C. |
| C$_4$H$_{9(n)}$ | C$_3$H$_{7(i)}$ | C$_3$H$_{7(i)}$ | 4-OCH$_3$ | H | m.p.: 143–144° C. |
| C$_6$H$_{13(n)}$ | C$_3$H$_{7(i)}$ | C$_3$H$_{7(i)}$ | H | H | |
| C$_7$H$_{15(n)}$ | C$_3$H$_{7(i)}$ | C$_3$H$_{7(i)}$ | H | H | |
| C$_{10}$H$_{21(n)}$ | C$_3$H$_{7(i)}$ | C$_3$H$_{7(i)}$ | H | H | |
| C$_4$H$_9$(tert.) | CH$_3$ | C$_3$H$_{7(i)}$ | 4-Cl | H | |
| —CH(CH$_2$CH$_2$) (cyclopropyl) | CH$_3$ | C$_4$H$_9$(tert.) | 4-Cl | H | |
| C$_4$H$_9$(tert.) | CH$_3$ | C$_4$H$_9$(tert.) | 4-Cl | H | |
| C$_2$H$_5$ | C$_2$H$_5$ | C$_4$H$_9$(sec.) | 4-Cl | H | |
| C$_3$H$_{7(n)}$ | C$_2$H$_5$ | C$_4$H$_9$(sec.) | 4-Cl | H | |
| C$_3$H$_{7(i)}$ | C$_2$H$_5$ | C$_4$H$_9$(sec.) | 4-Cl | H | |
| —CH(CH$_2$CH$_2$) (cyclopropyl) | C$_2$H$_5$ | C$_4$H$_9$(sec.) | 4-Cl | H | |

-continued

| R' | R" | R''' | $R^{IV}$ | $R^V$ |
|---|---|---|---|---|
| $C_4H_{9(n)}$ | $C_2H_5$ | $C_4H_9(sec.)$ | 4-Cl | H |
| $C_4H_{9(i)}$ | $C_2H_5$ | $C_4H_9(sec.)$ | 4-Cl | H |
| $C_4H_9(sec.)$ | $C_2H_5$ | $C_4H_9(sec.)$ | 4-Cl | H |
|  | $C_2H_5$ | $C_4H_9(sec.)$ | 4-Cl | H |
|  | $C_2H_5$ | $C_4H_9(sec.)$ | 4-Cl | H |
| $C_4H_9(tert.)$ | $C_3H_{7(i)}$ | $C_3H_{7(i)}$ | 4-Cl; 3-Cl | H |

(d) Production of the final product 11.54 g of N-2,6-diisopropyl-4-(phenoxyphenyl)-N'-tert-butylthiourea are dissolved in 30 ml of dimethyl formamide, and 5.96 g of methyl iodide are added dropwise to this solution at 40° C. The reaction mixture is allowed to stand for 12 hours at room temperature, then poured into an aqueous solution which is adjusted to and kept at pH 12 with potassium carbonate. The aqueous solution is extracted with methylene chloride and the organic phase is separated and dried over potassium carbonate. The methylene chloride is removed by distillation. Recrystallisation from hexane (cooling to −50° C.) yields the compound of the formula

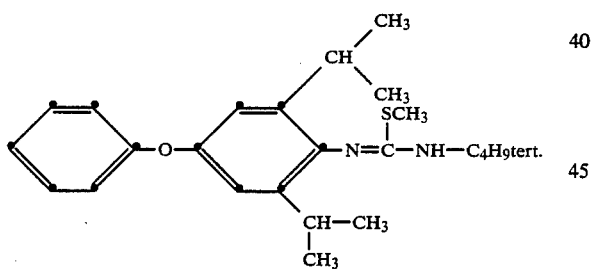

with a melting point of 89°–92°C.

The following compounds are also obtained in analogous manner:

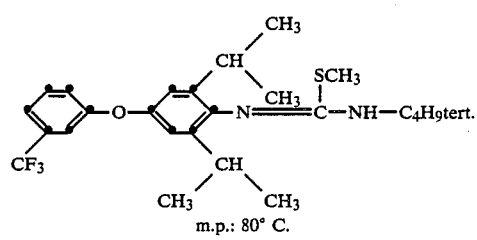

m.p.: 80° C.

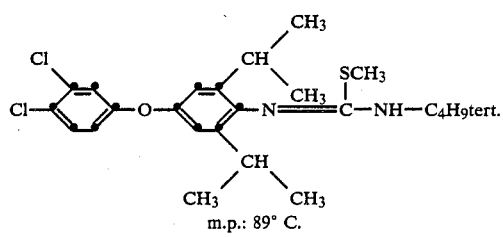

m.p.: 89° C.

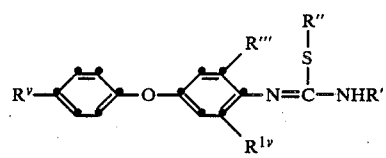

| R' | R" | R''' | $R^{IV}$ | $R^V$ | |
|---|---|---|---|---|---|
| $C_4H_9(tert.)$ | $CH_3$ | $C_3H_{7(i)}$ | $C_3H_{7(i)}$ | Cl | m.p.: 120° C. |
| $C_4H_9(tert.)$ | $CH_3$ | $C_3H_{7(i)}$ | $C_3H_{7(i)}$ | $CH_3$ | m.p.: 86–87° C. |
| $C_3H_{7(i)}$ | $CH_3$ | $C_3H_{7(i)}$ | $C_3H_{7(i)}$ | $CH_3$ | m.p.: 94–96° C. |
| $C_3H_{7(i)}$ | $CH_3$ | $C_3H_{7(i)}$ | $C_3H_{7(i)}$ | H | $n_D^{37,5°} = 1.5605$ |
| $C_3H_{7(i)}$ | $CH_3$ | $C_3H_{7(i)}$ | $C_3H_{7(i)}$ | $OCH_3$ | m.p.: 106–107° C. |
| $C_3H_{7(i)}$ | $C_2H_5$ | $C_3H_{7(i)}$ | $C_3H_{7(i)}$ | $OCH_3$ | m.p.: 67–68° C. |
| $C_4H_9(tert.)$ | $CH_3$ | $C_3H_{7(i)}$ | $C_3H_{7(i)}$ | $OCH_3$ | m.p.: 93–94° C. |
| $C_4H_9(tert.)$ | $C_2H_5$ | $C_3H_{7(i)}$ | $C_3H_{7(i)}$ | $OCH_3$ | m.p.: 114–116° C. |
| $C_4H_9(tert.)$ | $CH_3$ | $CH_3$ | $C_3H_{7(i)}$ | Cl | m.p.: 99–100° C. |
| 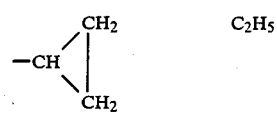 | $C_2H_5$ | $CH_3$ | $C_3H_{7(i)}$ | Cl | |

-continued

| R' | R'' | R''' | R$^{IV}$ | R$^V$ | |
|---|---|---|---|---|---|
| C$_4$H$_9$(tert.) | CH$_3$ | CH$_3$ | C$_4$H$_9$(tert.) | Cl | |
| C$_4$H$_9$(tert.) | —CH$_2$—C≡CH | CH$_3$ | C$_4$H$_9$(tert) | Cl | |
| —CH(CH$_2$)$_2$ (cyclopropyl) 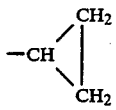 | CH$_3$ | C$_2$H$_5$ | C$_3$H$_{7(i)}$ | Cl | |
| —CH(CH$_2$)$_2$ (cyclopropyl) 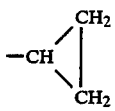 | C$_2$H$_5$ | C$_2$H$_5$ | C$_3$H$_{7(i)}$ | Cl | |
| C$_4$H$_9$(tert.) | CH$_3$ | C$_2$H$_5$ | C$_3$H$_{7(i)}$ | Cl | m.p.: 65–68° C. |
| C$_4$H$_9$(tert.) | —CH$_2$—C≡CH | C$_2$H$_5$ | C$_3$H$_{7(i)}$ | Cl | |
| —CH(CH$_2$)$_2$ (cyclopropyl) 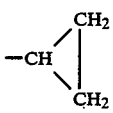 | CH$_3$ | CH$_3$ | C$_3$H$_{7(i)}$ | Cl | |
| C$_3$H$_{7(i)}$.HI | CH$_3$ | C$_3$H$_{7(i)}$ | C$_3$H$_{7(i)}$ | CH$_3$ | m.p.: 189–190° C. |
| C$_4$H$_9$(sec.) | CH$_3$ | C$_3$H$_{7(i)}$ | C$_3$H$_{7(i)}$ | CH$_3$ | |
| C$_4$H$_9$(tert.) | —CH$_2$—CH≡CH$_2$ | C$_3$H$_{7(i)}$ | C$_3$H$_{7(i)}$ | CH$_3$ | m.p.: 84–86° C. |
| C$_4$H$_9$(tert.).HI | CH$_3$ | C$_3$H$_{7(i)}$ | C$_3$H$_{7(i)}$ | CH$_3$ | m.p.: 169–170° C. |
| C$_4$H$_9$(tert.) | C$_2$H$_5$ | C$_3$H$_{7(i)}$ | C$_3$H$_{7(i)}$ | CH$_3$ | m.p.: 111–113° C. |
| C$_4$H$_9$(tert.).HBr | —CH$_2$—CH=CH$_2$ | C$_3$H$_{7(i)}$ | C$_3$H$_{7(i)}$ | CH$_3$ | m.p.: 124–126° C. |
| CH$_3$ | CH$_3$ | C$_3$H$_{7(i)}$ | C$_3$H$_{7(i)}$ | OCH$_3$ | m.p.: 120–121° C. |
| CH$_3$.HI | CH$_3$ | C$_3$H$_{7(i)}$ | C$_3$H$_{7(i)}$ | OCH$_3$ | m.p.: 176–177° C. |
| C$_2$H$_5$ | CH$_3$ | C$_3$H$_{7(i)}$ | C$_3$H$_{7(i)}$ | OCH$_3$ | m.p.: 100–102° C. |
| C$_2$H$_5$.HI | CH$_3$ | C$_3$H$_{7(i)}$ | C$_3$H$_{7(i)}$ | OCH$_3$ | m.p.: 176–177° C. |
| C$_3$H$_{7(n)}$ | CH$_3$ | C$_3$H$_{7(i)}$ | C$_3$H$_{7(i)}$ | OCH$_3$ | m.p.: 76–77° C. |
| C$_3$H$_{7(n)}$.HI | CH$_3$ | C$_3$H$_{7(i)}$ | C$_3$H$_{7(i)}$ | OCH$_3$ | m.p.: 171–172° C. |
| C$_3$H$_{7(i)}$ | CH$_3$ | C$_3$H$_{7(i)}$ | C$_3$H$_{7(i)}$ | OCH$_3$ | m.p.: 106–107° C. |
| C$_4$H$_{9(n)}$ | CH$_3$ | C$_3$H$_{7(i)}$ | C$_3$H$_{7(i)}$ | OCH$_3$ | m.p.: 70–72° C. |
| C$_4$H$_{9(n)}$.HI | CH$_3$ | C$_3$H$_{7(i)}$ | C$_3$H$_{7(i)}$ | OCH$_3$ | m.p.: 142–145° C. |
| C$_4$H$_{9(i)}$ | CH$_3$ | C$_3$H$_{7(i)}$ | C$_3$H$_{7(i)}$ | OCH$_3$ | m.p.: 111–112° C. |
| C$_4$H$_{9(i)}$.HI | CH$_3$ | C$_3$H$_{7(i)}$ | C$_3$H$_{7(i)}$ | OCH$_3$ | m.p.: 136–140° C. |
| C$_4$H$_9$(sec.) | CH$_3$ | C$_3$H$_{7(i)}$ | C$_3$H$_{7(i)}$ | OCH$_3$ | m.p.: 83–84° C. |
| C$_4$H$_9$(sec.).HI | CH$_3$ | C$_3$H$_{7(i)}$ | C$_3$H$_{7(i)}$ | OCH$_3$ | |
| C$_7$H$_{15(n)}$ | CH$_3$ | C$_3$H$_{7(i)}$ | C$_3$H$_{7(i)}$ | OCH$_3$ | n$_D^{35°}$: 1.5518 |
| C$_7$H$_{15(n)}$.H | CH$_3$ | C$_3$H$_{7(i)}$ | C$_3$H$_{7(i)}$ | OCH$_3$ | m.p.: 119–122° C. |
| CH$_3$ | CH$_3$ | C$_3$H$_{7(i)}$ | C$_3$H$_{7(i)}$ | H | m.p.: 109–110° C. |
| CH$_3$.HI | CH$_3$ | C$_3$H$_{7(i)}$ | C$_3$H$_{7(i)}$ | H | m.p.: 190–192° C. |
| C$_2$H$_5$ | CH$_3$ | C$_3$H$_{7(i)}$ | C$_3$H$_{7(i)}$ | H | m.p.: 75–76° C. |
| C$_2$H$_5$.HI | CH$_3$ | C$_3$H$_{7(i)}$ | C$_3$H$_{7(i)}$ | H | m.p.: 189–190° C. |
| C$_3$H$_{7(n)}$ | CH$_3$ | C$_3$H$_{7(i)}$ | C$_3$H$_{7(i)}$ | H | n$_D^{40°}$: 1.5650 |
| C$_3$H$_{7(n)}$ | CH$_3$ | C$_3$H$_{7(i)}$ | C$_3$H$_{7(i)}$ | H | m.p.: 190–191° C. |
| C$_3$H$_{7(i)}$.HI | CH$_3$ | C$_3$H$_{7(i)}$ | C$_3$H$_{7(i)}$ | H | m.p.: 183–184° C. |
| C$_4$H$_{9(n)}$ | CH$_3$ | C$_3$H$_{7(i)}$ | C$_3$H$_{7(i)}$ | H | n$_D^{50°}$: 1.5544 |
| C$_4$H$_{9(n)}$.HI | CH$_3$ | C$_3$H$_{7(i)}$ | C$_3$H$_{7(i)}$ | H | m.p.: 185–187° C. |
| C$_4$H$_{9(i)}$ | CH$_3$ | C$_3$H$_{7(i)}$ | C$_3$H$_{7(i)}$ | H | n$_D^{40°}$: 1.5569 |
| C$_4$H$_{9(i)}$.HI | CH$_3$ | C$_3$H$_{7(i)}$ | C$_3$H$_{7(i)}$ | H | m.p.: 170–171° C. |
| C$_4$H$_9$(sec.) | CH$_3$ | C$_3$H$_{7(i)}$ | C$_3$H$_{7(i)}$ | H | n$_D^{50°}$: 1.5512 |
| C$_4$H$_9$(sec.).HI | CH$_3$ | C$_3$H$_{7(i)}$ | C$_3$H$_{7(i)}$ | H | m.p.: 148–150° C. |
| C$_5$H$_{11(n)}$ | CH$_3$ | C$_3$H$_{7(i)}$ | C$_3$H$_{7(i)}$ | H | n$_D^{40°}$: 1.5548 |
| C$_5$H$_{11(n)}$.HI | CH$_3$ | C$_3$H$_{7(i)}$ | C$_3$H$_{7(i)}$ | H | m.p.: 139–141° C. |
| C$_6$H$_{13(n)}$ | CH$_3$ | C$_3$H$_{7(i)}$ | C$_3$H$_{7(i)}$ | H | n$_D^{40°}$: 1.5524 |
| C$_6$H$_{13(n)}$.HI | CH$_3$ | C$_3$H$_{7(i)}$ | C$_3$H$_{7(i)}$ | H | m.p.: 121–122° C. |
| C$_7$H$_{15(n)}$ | CH$_3$ | C$_3$H$_{7(i)}$ | C$_3$H$_{7(i)}$ | H | n$_D^{40°}$: 1.5461 |
| C$_7$H$_{15(n)}$.HI | CH$_3$ | C$_3$H$_{7(i)}$ | C$_3$H$_{7(i)}$ | H | m.p.: 100–101° C. |
| C$_{10}$H$_{21(n)}$ | CH$_3$ | C$_3$H$_{7(i)}$ | C$_3$H$_{7(i)}$ | H | n$_D^{40°}$: 1.5392 |
| C$_{10}$H$_{21(n)}$.HI | CH$_3$ | C$_3$H$_{7(i)}$ | C$_3$H$_{7(i)}$ | H | |
| CH$_3$ | CH$_3$ | C$_2$H$_5$ | C$_4$H$_9$(sec.) | Cl | |
| CH$_3$.HI | CH$_3$ | C$_2$H$_5$ | C$_4$H$_9$(sec.) | Cl | m.p.: 165–170° C. |
| CH$_3$ | C$_3$H$_{7(n)}$ | C$_2$H$_5$ | C$_4$H$_9$(sec.) | Cl | |
| C$_2$H$_5$ | CH$_3$ | C$_2$H$_5$ | C$_4$H$_9$(sec.) | Cl | n$_D^{40°}$: 1.5731 |
| C$_2$H$_5$.HI | CH$_3$ | C$_2$H$_5$ | C$_4$H$_9$(sec.) | Cl | m.p.: 140–145° C. |
| C$_2$H$_5$ | C$_4$H$_{9(n)}$ | C$_2$H$_5$ | C$_4$H$_9$(sec.) | Cl | |
| C$_3$H$_{7(n)}$ | CH$_3$ | C$_2$H$_5$ | C$_4$H$_9$(sec.) | Cl | n$_D^{40°}$: 1.5681 |
| C$_3$H$_7$.HI | CH$_3$ | C$_2$H$_5$ | C$_4$H$_9$(sec.) | Cl | m.p.: 87–90° C. |
| C$_3$H$_{7(n)}$.HI | —CH$_2$—C≡CH | C$_2$H$_5$ | C$_4$H$_9$(sec.) | Cl | n$_D^{40°}$: 1.5734 |
| C$_3$H$_{7(i)}$ | CH$_3$ | C$_2$H$_5$ | C$_4$H$_9$(sec.) | Cl | n$_D^{50°}$: 1.5528 |
| C$_3$H$_{7(i)}$.HI | CH$_3$ | C$_2$H$_5$ | C$_4$H$_9$(sec.) | Cl | m.p.: 130–135° C. |
| C$_3$H$_{7(i)}$ | —CH$_2$—CH=CH$_2$ | C$_2$H$_5$ | C$_4$H$_9$(sec.) | Cl | n$_D^{40°}$: 1.5631 |

-continued

| R' | R'' | R''' | R^IV | R^V | |
|---|---|---|---|---|---|
| -CH(CH₂)(CH₂) (cyclopropyl) | CH₃ | C₂H₅ | C₄H₉(sec.) | Cl | $n_D^{40°}$: 1.5721 |
| -CH(CH₂)(CH₂) (cyclopropyl) | C₂H₅ | C₂H₅ | C₄H₉(sec.) | Cl | $n_D^{40°}$: 1.5560 |
| C₄H₉(n) | CH₃ | C₂H₅ | C₄H₉(sec.) | Cl | |
| C₄H₉(n).HI | CH₃ | C₂H₅ | C₄H₉(sec.) | Cl | |
| C₄H₉(i) | CH₃ | C₂H₅ | C₄H₉(sec.) | Cl | $n_D^{50°}$: 1.5563 |
| C₄H₉(i).HI | CH₃ | C₂H₅ | C₄H₉(sec.) | Cl | $n_D^{40°}$: 1.5734 |
| C₄H₉(i) | —CH₂—C≡CH | C₂H₅ | C₄H₉(sec.) | Cl | |
| C₄H₉(sec.) | CH₃ | C₂H₅ | C₄H₉(sec.) | Cl | $n_D^{50°}$: 1.5562 |
| C₄H₉(sec.).HI | CH₃ | C₂H₅ | C₄H₉(sec.) | Cl | |
| C₄H₉(sec.) | —CH₂—CH=CH₂ | C₂H₅ | C₄H₉(sec.) | Cl | $n_D^{50°}$: 1.5547 |
| C₄H₉(tert.) | CH₃ | C₂H₅ | C₄H₉(sec.) | Cl | $n_D^{50°}$: 1.5591 |
| C₄H₉(tert.) | —CH₂—C≡CH | C₂H₅ | C₄H₉(sec.) | Cl | $n_D^{50°}$: 1.5596 |
| cyclohexyl-H | CH₃ | C₂H₅ | C₄H₉(sec.) | Cl | $n_D^{50°}$: 1.5643 |
| cyclohexyl-H .HI | CH₃ | C₂H₅ | C₄H₉(sec.) | Cl | |
| cyclohexyl-H | —CH₂C≡CH | C₂H₅ | C₄H₉(sec.) | Cl | $n_D^{50°}$: 1.5721 |
| C₄H₉(tert.) | C₂H₅ | C₃H₇(i) | C₃H₇(i) | H | $n_D^{50°}$: 1.5750 |
| C₄H₉(tert.) | C₂H₅.HI | C₃H₇(i) | C₃H₇(i) | H | |
| C₄H₉(tert.) | C₃H₇(n) | C₃H₇(i) | C₃H₇(i) | H | m.p.: 62–63° C. |
| C₄H₉(tert.) | C₃H₇(n).HI | C₃H₇(i) | C₃H₇(i) | H | |
| C₄H₉(tert.) | C₄H₉(n) | C₃H₇(i) | C₃H₇(i) | H | m.p.: 57–60° C. |
| C₄H₉(tert.) | C₄H₉.HBr | C₃H₇(i) | C₃H₇(i) | H | |
| C₄H₉(tert.) | C₄H₉(i) | C₃H₇(i) | C₃H₇(i) | H | m.p.: 80–82° C. |
| C₄H₉(tert.) | C₄H₉(i).HI | C₃H₇(i) | C₃H₇(i) | H | $n_D^{40°}$: 1.5672 |
| C₄H₉(tert.) | —CH₂—CH=CH₂ | C₃H₇(i) | C₃H₇(i) | H | m.p.: 78–80° C. |
| C₄H₉(tert.) | —CH₂CH=CH₂.HBr | C₃H₇(i) | C₃H₇(i) | H | |
| C₄H₉(tert.) | —CH₂—C≡CH | C₃H₇(i) | C₃H₇(i) | H | m.p.: 79–81° C. |
| C₄H₉(tert.) | —CH₂C≡HBr | C₃H₇(i) | C₃H₇(i) | H | |
| C₃H₇(i) | —CH₂CH=CH₂ | C₃H₇(i) | C₃H₇(i) | H | |
| C₃H₇(i) | —CH₂—CH=CH₂.HBr | C₃H₇(i) | C₃H₇(i) | H | m.p.: 171–172° C. |
| C₄H₉(tert.) | CH₃ | C₂H₅ | C₄H₉(sec.) | H | $n_D^{40°}$: 1.5549 |
| C₃H₇(i) | CH₃ | C₂H₅ | C₄H₉(sec.) | H | $n_D^{30°}$: 1.5662 |

EXAMPLE 2

Insecticidal stomach-poison action: *Spodoptera littoralis, Heliothis virescens* and *Dysdercus fasciatus*

Cotton plants are sprayed with an aqueous emulsion containing 0.05% of the compound to be tested (obtained from a 10% emulsifiable concentrate).

After the spray coating has dried, the plants are populated with larvae of the species *Spodoptera littoralis* (L3 stage), *Dysdercus fasciatus* (L4 stage) or *Heliothis virescens* (L3 stage). Two plants are used for each test compound and insect species. A mortality count is made after 2, 4, 24 and 48 hours. The test is carried out at 24° C. and 60% relative humidity. In this test, the compounds of Example 1 are very effective against larvae of the species *Spodoptera littoralis, Dysdercus fasciatus* and *Heliothis virescens*.

EXAMPLE 3

Insecticidal stomach poison action against *Leptinotarsa decemlineata*

The method described in Example 2 is repeated, using potato plants instead of cotton plants and larvae of the species *Leptinotarsa decemlineata* in the L3 stage. In this test also, the compounds of Example 1 are effective against larvae of the above species.

EXAMPLE 4

Action against plant-destructive acarids (mites) *Tetranychus urticae* (OP-sensitive) and *Tetranychus cinnabarinus* (OP-tolerant)

16 hours before the test for acaricidal action, the primary leaves of *Phaseolus vulgaris* plants are infected with an infested piece of leaf from a mass culture of *Tetranychus urticae* (OP-sensitive) or *Tetranychus cinnabarinus* (OP-tolerant). (The tolerance refers to the tolerance to diazinone). The treated, infested plants are sprayed with a test solution containing 400 or 200 ppm of the compound to be tested. A count of the number of living and dead imagines and larvae (all mobile stages) is made under a stereoscopic microscope after 24 hours and again after 7 days. One plant is used for each test substance and test species. During the test run, the plants are kept in greenhouse compartments at 25° C.

In the above test, the compounds of formula I are effective against adults and larvae of the species *Tetranychus urticae* and *Tetranychus cinnabarius*.

EXAMPLE 5

Action against ectoparasitic acarids (ticks: *Rhipicephalus bursa* (imagines and larvae), *Amblyomma hebraeum* (♀ imagines, nymphs and larvae) and *Boophilus microplus* (larvae, OP-sensitive and OP-tolerant)

The test organisms employed are about 50 larvae, about 25 nymphs or about 10 imagines of each of the tick species *Rhipicephalus bursa*, *Amblyomma hebraeum* and *Boophilus microplus*. The test organisms are immersed briefly in an aqueous emulsion or solution containing 0.1, 1.0, 10, 50 or 100 ppm of the respective compound. The emulsions or solutions in test tubes are then absorbed by cotton wool and the wetted test organisms are kept in the contaminated tubes. A mortality count at each concentration is made after 3 days (larvae) and 14 days (nymphs and imagines).

Compounds of the formula I are effective in this test against larvae, nymphs and imagines of *Rhipicephalus bursa* and *Amblyomma hebraeum* and against larvae (OP-resistant and OP-sensitive) of *Boophilus microplus*.

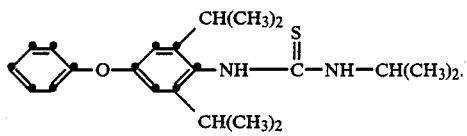

What is claimed is:

1. A compound of the formula

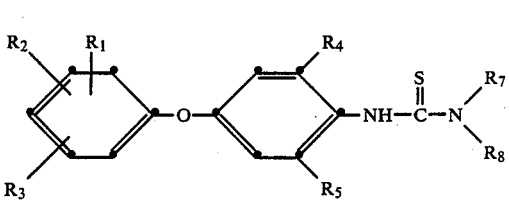

wherein each of $R_1$, $R_2$ and $R_3$ is hydrogen, halogen, $C_1$-$C_4$-alkyl, $C_1$-$C_4$-alkoxy, trifluoromethyl or nitro; each of $R_4$ and $R_5$ is isopropyl, isobutyl, or tertiary butyl; $R_7$ is propyl or butyl; and $R_8$ is hydrogen.

2. A compound according to claim 1 wherein $R_4$ and $R_5$ are each isopropyl and $R_7$ is isopropyl or tertiary butyl.

3. A compound according to claim 1 wherein $R_1$, $R_2$ and $R_3$ are each hydrogen.

4. A compound according to claim 2 wherein $R_1$ is halogen in the 4-position and $R_2$ and $R_3$ are each hydrogen.

5. A compound according to claim 2 wherein $R_1$ is trifluoromethyl in the 3-position and $R_2$ and $R_3$ are each hydrogen.

6. A compound according to claim 2 wherein $R_1$ and $R_2$ are chlorine in the 3- and 4-positions and $R_3$ is hydrogen.

7. The compound according to claim 3 of the formula

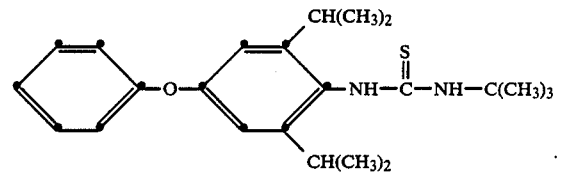

8. The compound according to claim 3 of the formula